United States Patent [19]

Martin et al.

[11] Patent Number: 4,550,082
[45] Date of Patent: Oct. 29, 1985

[54] PROCESS FOR THE DETECTION AND THE QUALITATIVE AND QUANTITATIVE DIFFERENTIATION OF NATURALLY DEUTERATED MOLECULES AND APPLICATION THEREOF MORE ESPECIALLY TO THE DETECTION OF CHAPTALIZATION OF WINES

[75] Inventors: Gérard J. Martin; Maryvonne L. Martin, both of Nantes, France

[73] Assignee: Centre National de la Recherche Scientifique, Paris, France

[21] Appl. No.: 446,049

[22] Filed: Dec. 1, 1982

[30] Foreign Application Priority Data

Dec. 4, 1981 [FR] France ............................ 81 22710

[51] Int. Cl.[4] ...................... G01N 24/00; G01N 33/14
[52] U.S. Cl. ..................................... 436/24; 436/132; 436/139; 436/173; 436/177; 426/592
[58] Field of Search ........................ 436/24, 173–176, 436/8, 132, 139, 177; 324/300, 308, 307; 426/231, 592

[56] References Cited

U.S. PATENT DOCUMENTS 3,915,641  9/1975  Goering et al. ...................... 437/173
4,206,132  6/1980  Sievers ............................. 260/429.2

FOREIGN PATENT DOCUMENTS 2475736  8/1981  France .
0732742  5/1980  U.S.S.R. ............................... 436/24

OTHER PUBLICATIONS

"Application of Nuclear Magnetic Resonance to Quantitative Analysis of Mixtures of Organic Peroxides, Hydroperoxides, and Alcohols", Ward et al., Analytical Chemistry, vol. 41, No. 3, Mar. 1969, 538–540.

"Organic Chemistry", 3rd Edition Text, Morrison and Boyd, 1973.

Sov. Phys.–Jetp, vol. 42, No. 6, Dec. 1975–"NMR Study of Hydrogen Isotopes to Determine the Ratio of the Proton and Deuteron Magnetic Moments to the Eighth Decimal Place", pp. 950–954.

Z. Naturforsch, vol. 34c, Nov. 2, 1978–Rauschenbach et al.; "Vergleich der Deuterium- und Kohlenstoff-1-3-Gehalte in Fermentations- und Syntheseethanol", pp. 1–4.

"Manuel de Resonance Magnetique Nucleaire", (1971), R. Freymann et al., pp. 132-137.

C.R. Acad. Sc. Paris, t. 293 (1981), Gerard J. Martin et al., "Chimie Physique Atomique et Moleculaire", pp. 31-33.

European Search Report of EP 82 40 2209.

Primary Examiner—Barry S. Richman
Assistant Examiner—Joseph P. Carrier
Attorney, Agent, or Firm—Oblon, Fisher, Spivak, McClelland & Maier

[57] ABSTRACT

A process is provided for the detection and qualitative and quantitive differentiation of naturally deuterated molecules.

This process consists in (a) preparing a standard by mixing a commercially available hydrocarbonic product with its artificially deuterated analogue, (b) introducing this standard into the measuring cell of the RMN analysis apparatus; (c) adding the product to be analyzed to the cell and (d) introducing the cell into the RMN (D) apparatus and recording the spectrum of the deuterium which is compared with the RMN (D) spectra of products of known geographical origin and from known chemical and/or biochemical sources, made beforehand with the same standard.

16 Claims, 7 Drawing Figures

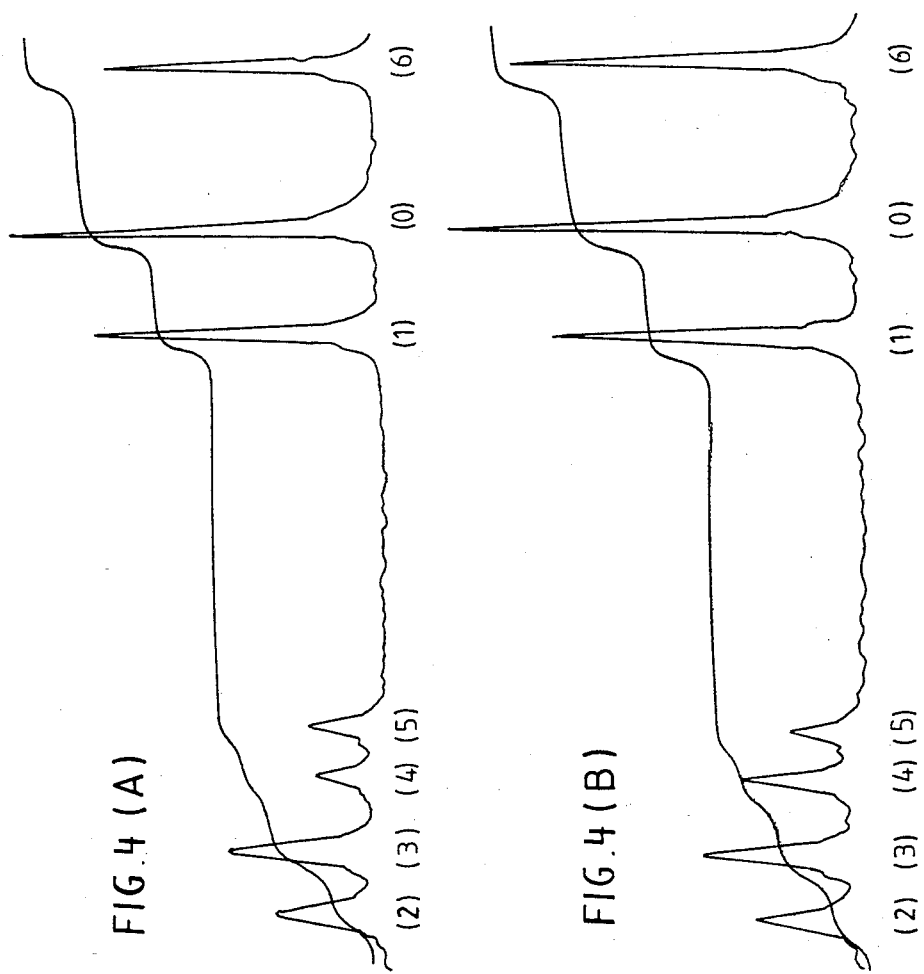
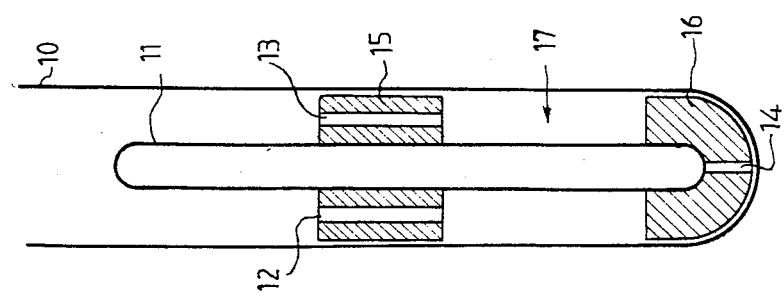

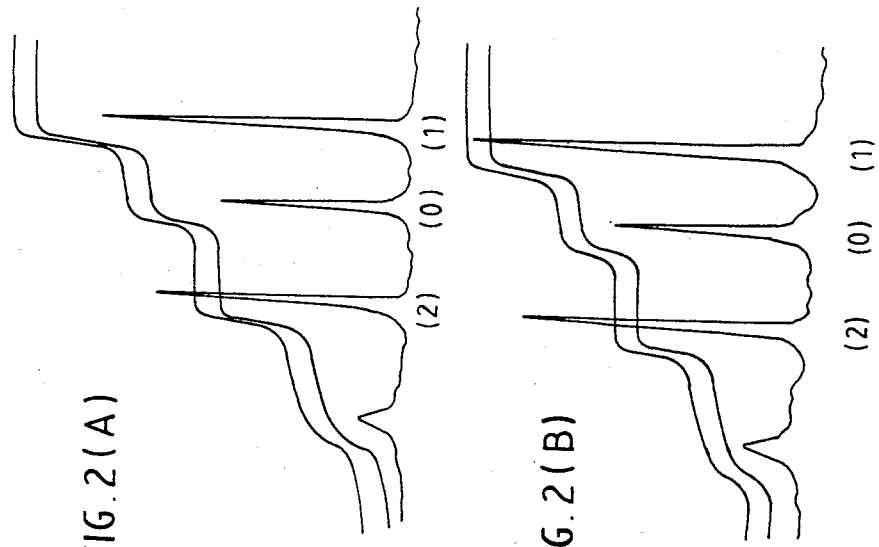
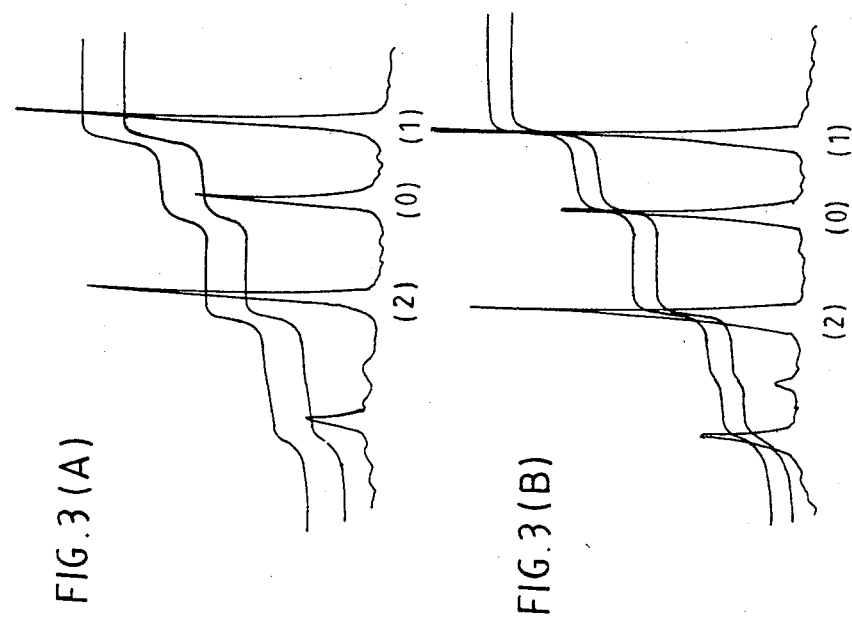

PROCESS FOR THE DETECTION AND THE QUALITATIVE AND QUANTITATIVE DIFFERENTIATION OF NATURALLY DEUTERATED MOLECULES AND APPLICATION THEREOF MORE ESPECIALLY TO THE DETECTION OF CHAPTALIZATION OF WINES

BACKGROUND OF THE INVENTION

The present invention relates to a novel process for the detection and qualitative and quantitative differentiation of naturally deuterated molecules, as well as a device for implementing this process.

DESCRIPTION OF THE PRIOR ART

Deuterium D (the natural isotope of hydrogen) is widely spread since it practically always accompanies hydrogen.

If on Earth, its mean distribution is very small (of the order of 0.015%, i.e. 150 ppm), it is however subject to considerable fluctuations because of different isotopic fractionation factors of geological, geographical, climato-logival, physical, chemical and biochemical origin which occur in the history of a molecule.

The international standard, defined in VIENNA, is a sample of ocean water (Standard Mean Ocean Water or SMOW) which contains 155.78 ppm of D/H. On the other hand, water taken from the Antarctic ice (Standard Light Antarctic Precipitation) only contains 89.0 ppm of deuterium, i.e.—42.8%. Thus, most of the molecules contain variable quantities of deuterium. For example, sugars are in general very rich in SMOW (D/H=155 to 175 ppm), but their fermentation products, particularly ethanol, are very poor (D/H=135 to 115 ppm). Lipids are also poor in deuterium with respect to SMOW, and menthol contains no more than 90 ppm of deuterium.

The origin of these variations, as well as the mechanisms which govern them are not yet well known. This is not surprizing if we consider that the only method for measuring up to now the overal deuterium contents, mass spectrography, is a destructive technique which requires combustion of the sample and transformation into water of all the hydrogen atoms.

To be able then to measure accurately the amount of D present in a molecule, is to be able to determine its geographical, chemical, biological, climatological origin etc. Since, on the other hand, most of the molecules have a plurality of hydrogen atoms (and from its natural isotope, deuterium which is formed from a proton and a neutron), to be able to determine the intramolecular deuterium rates is to be able to draw up a veritable identity card of a molecule, and recognize with very great precision its origin.

The applications of this process may be countless: besides detecting the chaptalization of wines based on the recognition of the origin of the ethanol present in the wine, there may also be mentioned:

recognition of the origin of vodkas, whiskies, gins, and cereal and fodder plant spirits, the recognition of the origin of rums, marcs, brandies, fruit spirits, checking the geographical origin of anathols and estragols, checking the geographical origin of mineral oil, differentiation of rubbers (between synthetic rubber and natural rubber), determination of the geographical origin of water, etc.

In fact, determination of the biological, chemical or geographical origin of molecules, for example or ethyl alcohol, formed up to present an unsolved or very poorly solved problem. Thus:

H. SIMON and Collab. [Lebensmittel Forsch. p. 136 (1975)] advocated radioactive carbon 14 marking, which marking allowed identification to be made in some cases.

J. BRICOUT [Rev. Cytol. Biol. Veget. Bot. 1, 133(1978)] and

A. RAUSCHENBACK and Collab. [Z. Naturforsch. 34c, p. 1 (1979)] demonstrated that it is also possible under some conditions to measure by mass spectrometry the mean statistical deuterium ($^2H$), oxygen($18_O$), and carbon ($^{13}C$) content of all the ethanol molecule, which allows a distinction to be made between synthetic ethanol and natural ethanol.

In so far as chaptalization is concerned, the process called "dry extract" (decree of 19th Apr. 1898 and article 8 of the Wine Code) was used to try and detect overfortified wines. When the ratio of the alcohol content to that of the reduced extract is greater than 4.6 (red wines) or 6.5 (white wines), the corresponding wines were presumed to be overfortified. This process was taken up in a slightly different form in a ruling of the E.E.C. no. 2984 of 1978 (JOCE L 360 of 22nd Dec. 1978, p. 31). It is in this case a question of the densimetric alcohol/dry extract ratio. However, it is possible today to state, after several years of practice, that all these processes are not reliable and practically not reproducible. On the other hand, it is at present impossible to distinguish the natural origin of ethanols coming from the fermentation of different plants containing polysaccharides (diverse cereals, beets, potatoes, various fruits, etc.). Consequently, the quantitative estimation of mixtures of these alcohols is impossible. The same goes for the quantity determination of synthetic alcohols with respect to natural alcohols. Though we may make the distinction by mass spectrometry, the quantity determination is lacking in precision. Moreover, the procedure used is long and tiresome.

The low natural abundance of deuterium explains the fact that this nucleus is $10^6$ times more difficult to detect than the proton, for an equal sample volume. This is why the use of high field spectrometers with a superconducting coil of large diameter is required. This is however not a sufficient condition for effecting significant and reproducible quantitative measurements, which is precisely the aim of the present invention

SUMMARY OF THE INVENTION

The present invention provides a process for the detection and qualitative and quantitative differentiation of naturally deuterated molecules, characterized in that:

(a) a standard is prepared by mixing a commercially available hydrocarbonic product with its analogue artificially deuterated to 95-99%, so that the overall deuteration rate of the mixture is between 0.01 and 0.2%;

(b) this standard is introduced into a measuring cell of the nuclear magnetic resonance analysis apparatus (RMN), said cell being formed so that it may receive the standard so that there is no mixing between this standard and the product to be analyzed, (c) the product to be analyzed is added to the cell, and (d) the cell is introduced into the RMN (D) apparatus and the spectrum of the deuterium is recorded which is compared with the RMN (D) spectrum of products of known geographical origin and chemical and/or biochemical sources, made beforehand with the same standard.

According to an advantageous embodiment of the invention, the standard may comprise an intramolecular reference in the case of alcohols, which reference is chemically combined with the alcohol and the resulting product is introduced into the cell in accordance with step (b) above.

According to another advantageous embodiment of the invention, the enantiomeric purity of alcohols is determined by combining them with an optically active compount and this new compound is introduced into the cell in accordance with step (b) above.

According to an advantageous embodiment of the process of the invention, the standard is chosen from the products of the group comprising tetramethylsilane, hexamethyldisilane, hexamethyldisiloxane, hexamethyldisilazane, dimethyl-4,4-silapentane-4-sodium sulfonate, dimethyl-4,4-silapentane-4-sodium carboxylate, octamethylcyclotetrasiloxane, tetrakis(trimethylsilyl)methane, acetonitrile, acetone, benzene, dimethylsulfoxyde and chloroform.

According to a particularly advantageous embodiment of the invention, the intramolecular reference may be formed from acetic anhydride and/or acetic acid and/or acetyl chloride and/or acetyl bromide, the resulting product is then ethyl acetate.

According to a particularly advantageous embodiment of the invention, the optically active compound is formed from camphanic acid and/or malic acid and/or aspartic acid and/or proline and/or phenylalanine, to which small amounts of chelates are added.

According to another advantageous embodiment of the process of the invention, to the standard and/or to the sample to be analyzed are added small quantities of chromium and/or iron and/or cobalt and/or nickel and/or europium and/or praseodyme and/or ytterbium and/or dysprosium and/or holmium and/or erbium chelates.

According to a particular mode of this embodiment, the preceding chelates are prepared from a dione of the general formula I hereafter:

$$R'-C-CH_2-C-R \quad \quad (I)$$
$$\phantom{R'-}\|\phantom{-CH_2-}\|$$
$$\phantom{R'-}O\phantom{-CH_2-}O$$

in which:
R represents: $CH_3, tC_4H_9, nC_3F_7, C_2F_5, CF_3, tC_4D_9$ and
R' represents: $CH_3, tC_4H_9, CF_3, nC_3F_7, C_2F_5, nC_3H_7$.

The accuracy of the RMN measurements may be increased if a catalyst is added which promotes exchange of the hydroxyl sites of water and alcohol. In fact, the phenomenon of the chemical exchange of hydroxyl protons and deuterons must be carefully considered: the least trace of $H_3O^+$ ions catalyses this exchange, and the result is variations in the width of the spectral lines of the OD sites. This chemical change may indirectly affect the width of the CHD spectral lines, for relaxation of the methylene deuterium is likely to depend also on the exchange speed (relaxation by scalar coupling) which forms a source of inaccuracy.

The exchange speed itself depends on the purity of the alcohol, conditioned by the sampling method used.

In accordance with the invention, and in the case where the analysis relates to wines for detecting the rates of the naturally deuterated ethanol molecules, distillation is carried out beforehand after neutralization to pH 7.5 with an alkali.

According to another embodiment of the process of the invention, the sample is dehydrated on $CaH_2$ and the humid alcohols are distilled by liquid nitrogen cryotrapping.

According to another embodiment of the process of the invention, there is added to the sample between 0.01 and 1% vol/vol of an acid taken from the group comprising hydrochloric acid, nitric acid, sulfuric acid, phosphoric acid, trichloroacetic acid and perchloric acid.

The present invention also relates to an RMN measuring cell, characterized in that it is formed from two coaxial tubes insulated from each other, and whose

ratio is between 2.5:1 and 3.5:1. The inner tube maintained secured firmly to the outer tube by securing seals is intended to receive the standard, and may be sealed after introduction thereof, whereas the outer tube is intended to receive the substance to be analyzed. This latter is introduced into the lower part of said outer tube through an orifice formed in the securing seal which holds the two tubes together.

In a particularly advantageous embodiment of the cell of the invention, it is provided with a guide graduated and calibrated as a function of the spectrometer used, which guide allows the height of the turbine on the outer tube to be adjusted depending on the amount of the substance contained in the lower part of this outer tube.

According to another advantageous embodiment of the cell of the invention, the two coaxial tubes are made from gauged Pyrex glass.

According to the invention, the securing seals are two in number, the lower one holding the inner tube in place at its base and the upper one holding the inner tube in place at its middle.

According to an advantageous embodiment of the invention, the two securing seals are formed from two cylindrical Teflon blocks.

According to another advantageous embodiment of the invention, the two blocks are pierced: the upper block with two orifices, one for introducing the substance to be analyzed and the other for letting the air escape, whereas the lower block is pierced with one orifice for fixing the inner tube containing the standard substance. Cylindrical grooves are further machined in said blocks, so as to provide easy sliding thereof in the outer tube.

According to a particularly advantageous embodiment of the invention, two hollow threaded rods integral with each other may be fitted to the upper securing block so as to adjust exactly the levelling of the substance to be analyzed contained in the lower part of the outer tube, with the lower surface of said securing block.

In accordance with the invention, the diameter of the coaxial tubes is between 10 and 50 mm for the outer tube and between 4 and 12 mm for the inner tube.

In addition to the preceding araangements, the invention comprise other arrangements which will become clear from the following description.

BRIEF DESCRIPTION OF THE DRAWINGS

The invention will be better understood from the complement of description which follows, which refers to examples of implementing the process of the present invention by means of a device which also forms the subject of the present invention, which device is shown schematically, by way of non limiting example, in the accompanying drawings.

BRIEF DESCRIPTION OF THE DRAWINGS

FIG. 1 shows a measuring cell according to the present invention.

FIGS. 2a and 2b show the spectra of maize (A) and beet (B) alcohols.

FIGS. 3a and 3b show the spectra of two white wines, A (unchaptalized) and B (chaptalized).

FIGS. 4a and 4b represent the spectra of two anethols, A (natural) and B (synthetic).

It should however be understood that the examples described hereafter, the representation of the parameters used as well as the device described in what follows and shown in the drawings, are given solely by way of illustration of the subject of the invention, but form in no wise a limitation thereof.

DESCRIPTION OF THE PREFERRED EMBODIMENTS

(1) Representation of the parameters used

The RMN spectrum of the deuterium of a given sample is formed from several signals (i); the standard substance gives a single signal (o). The intensity of a signal should then be expressed by means of a precise parameter. In what follows the heights of the signals h(i) have been used, when the mid-height widths are equal,(or constant), for the heights are accurately measurable. In the other cases, the integrated surfaces S(i) have been used. These two parameters form two different scales, but very closely correlated with each other. However, the height h(i) or the surface S(i) of a signal i may vary slightly from one spectrum to another, and it is necessary to then consider the D ratios $$D(i) = \frac{h(i)}{h(o)} \text{ and } D'(i) = \frac{S(i)}{S(o)}$$

which do not depend on the experimental conditions. h(o) and S(o) represent the standard signal.

The same goes for $$T = \sum_{i+1}^{n} D(i)$$

where n represents the number of different molecules in the mixture, and

T represents the overall rate.

(2) Study of an ethanol

The relative intermolecular rates of deuterium are defined in the following way. The reference signal is that of the methyl group to which a statistical weight of 3 has been attributed. Then the intensity of the methylene group h(CHD) is compared with that of the normalized intensity of the methyl group, i.e.

$$\frac{h(CH_2D)}{3};$$

the relative intramolecular rate R is then expressed by:

$$R_h(CHD) = \frac{3h(CHD)}{h(CH_2D)} \text{ and } R_s(CHD) = \frac{3 S(CHD)}{S(CH_2D)}$$

The indices h or S indicate that the heights or the integrated surfaces have been respectively used for representing the quantities of nucleii resonating at a given position.

In the case of the hydroxyl site, the surface $S_{OH}$ alone may be validly considered for, because of too large fluctuations of the spectrum line widths, the intensities are no longer directly comparable.

It will be noted that if the deuterium were distributed statistically in the molecule, the defined parameters would would be:

$R_h(CHD) = R_S(CHD) = 2$, which corresponds to the methylene/methyl distribution $= \frac{2}{3}$. A value 2.5 for example indicates then a considerable relative overpopulation of methylene (or underpopulation of methyl).

It should also be noted that if heights and surfaces of the signals were both exactly proportional to the number of nucleii resonating at the frequency considered, the ratios $R_h$ and $R_S$ would have to be equal. However, this equality requires the mid-height widths of the methyl and methylene spectral lines to be strictly equal, which may not be the case (the spectral line widths are governed by relaxation processes likely to take place at slightly different speeds in the two sites). The result is that the values of $R_h$ are often fairly considerably greater than the values of $R_S$.

The introductions of a standard substance into the inner coaxial tube allows comparison of the overall deuteration rates. This use of a reference allows the two other complementary parameters $R_h(Ref)$ and $R_S(Ref)$ to be defined.

$$R_h(Ref) = \frac{3 \, h(Ref)}{h(CH_2D)} \quad R_S(Ref) = \frac{3 \, S(Ref)}{S(CH_2D)}$$

as well as a relative overall rate $$T_S = \frac{S(CH_2D) + S(CHD) + S(OD)}{S(Ref)}$$

With these values, the variation of the partial (R) or overall (T) deuterium rate may be compared from one sample to another.

Another way of measuring the overall deuterium rate of an ethanol molecule without being troubled by the contribution of the deuterated molecules containing sites exchangeable with water ($CH_3CH_2OD$), is to use an intramolecular reference. The alcohol samples to be compared are transformed into ethyl acetate by reaction with an excess of reference acetic anhydride (Ref) of controlled origin and known deuterium (D/H) content. The amount of $(D/H)_I$ and $(D/H)_{II}$ contents of the $CH_2DCH_2O_H$ and $CH_3CHDOH$ sites may then be easily determined with respect to that of the acetic anhydride by using the $R_h$ parameters which are accessible with great accuracy. We will then have:

$$R_h(CH_2D/Ref) = \frac{3h(CH_2D)}{h(Ref)}$$

$$R_h(CHD/Ref) = \frac{3h(CHD)}{h(Ref)}$$

(3) Physical representation of the relative intramolecular rates

The proton spectrum of ethanol is characterized by the triplet-quartet-singleton system (in the case of the rapid exchange of hydroxyl protons which generally takes place when the alcohols are imperfectly purified). This system corresponds to the real molecule $CH_3CH_2OH$.

The situation is very different when we consider naturally deuterated molecules for, because of the very low natural abundance of $^2H(0.015\%)$, there is a very small probability ($\simeq 2.10^{-8}$) for two deuterium atoms to be present in the same molecule. The RMN $^2H$ will then observe the signals of the following molecules:

| (1) | (2) | (3) |
|---|---|---|
| $CH_2DCH_2OH$ | $CH_3CHDOH$ | $CH_3CH_2OD$ |

Each of these three molecules is characterized by:
(1): $h_{(1)}$ $S_{(1)}$
(2): $h_{(2)}$ $S_{(S)}$
(3): $h_{(3)}$ $S_{(3)}$
Thus $$D_{(1)} = \frac{h(1)}{h(0)}, \quad D_{(2)} = \frac{h(2)}{h(0)}, \quad D_{(3)} = \frac{h(3)}{h(0)}$$

and the relative intramolecular rate $$R = \frac{3 D(2)}{D(1)}$$

Similarly, the overall rate is equal:

$$T = \frac{S(1) + S(2) + S(3)}{S(0)}$$

The deuterium rates defined could easily be converted into molar fractions of the different molecules (1), (2), (3). In fact, by calling fm(i) the molar fraction of the species i, we have:

$$fm(1) = \frac{S(CH_2D)}{\Sigma S} \quad fm(2) = \frac{S(CHD)}{\Sigma S} \quad fm(3) = \frac{S(OD)}{\Sigma S}$$

with $S = S(CH_2D) + S(CHD) + S(OD)$
(S always designates the surfaces of the specified signals).

The analogous expressions may be written for the intensities i, but they are not usable in this case, for the spectral OD line is much wider than the others. We can then see that $$R(CHD) = \frac{3fm(2)}{fm(1)}$$

It is possible to know the amount of deuterium present in each of the molecules (1), (2), (3) by multiplying the molar fractions fm(i) by the overall rate $T_S$.

(4) The relationship between the internal distribution of deuterium and the chaptalization rate of a wine (a) Remainder of the symbolism used Real molecules: $CH_2DCH_2OH$, $CH_3CHDOH$, $CH_3CH_2OD$
                     (1)              (2)              (3)

Intramolecular deuterium rate: $R = 3 \frac{A(2)}{A(1)}$

A may be either the height h, or the surface S.

| Origin of the ethanols: | wine: | V |
|---|---|---|
| | beet sugar: | B |
| | wine + beet sugar mixture: | M |

(b) Determination of the relationship between $R^M$ and $R^V$, $R^B$.

We will only consider the molecules (1) and (2). A wine alcohol and beet alcohol mixture will be defined by the molar fraction $F_D{}^B$, i.e.

$$F_D{}^B = (n_1{}^B + n_2{}^B)/(n_1{}^B + n_2{}^B) + (n_1{}^V + n_2{}^V)$$

$n_1{}^B$ the number of moles I coming from the beet, etc.
On the other hand, the intramolecular deuterium rate of the mixture $R^M$ is equal to:

$$\frac{3 A^M{}_{(2)}}{A^M{}_{(1)}}$$

namely:

$$R^M = 3 \frac{(n_2{}^V + n_2{}^B)}{(n_1{}^V + n_1{}^B)}$$

By arranging this equation, we find $$R^M = \frac{R^V}{1 + n_1{}^B/n_1{}^V} + \frac{R^B}{1 + n_1{}^V/n_1{}^B}$$

that is to say, taking into account the definition of the molar fraction F and of $a_D = Ta_H$ $$R^M = \frac{R^B + a_H TKR^V}{(1 + a_H TK)}$$

where T is the relative deuterium content of the beet alcohol with respect to the wine alcohol $$K = \frac{3 + R^V}{3 + R^B} \quad a_D = \frac{F_D{}^V}{F_D{}^B} \quad \text{and} \quad a_H = \frac{F_H{}^V}{F_H{}^B} \text{ (ratio expressed in volume)}$$

The variation of the function $R^M$ with $a_H$, for $R^V$ and $R^B$ fixed, is not linear, but does not deviate substantially ($\pm 1^\circ/_{oo}$) from linearity.

In a first approximation, we may consider that:

$$R^M = (1 - F_H{}^B)R^V + F_H{}^B R^B$$

(c) Application to the chaptalization rate of a wine

From the point of view of the RMN, a chaptalized wine may be considered as a mixture of deuterated ethanol (1), (2) and (3), a part of which comes from grapes and the other from beet. On the assumption of chaptalization with beet sugar).

If we call t the titre of the wine (in % volume)

c the chaptalization rate (in % volume), we may simply write:

$$F_H^B = c/t$$

Thus, the chaptalization rate c may be calculated as a function of t (easily measurable) and of $R^M$, $R^V$ and $R^B$.

$$c = \frac{tT(3 + R^B)(R^V - R^M)}{(3 + R^V)(R^M - R^B) + T(3 + R^B)(R^V - R^M)}$$

where, in a first approximation $$c = \frac{t(R^V - R^M)}{(R^V - R^B)}$$

Another representation of c causes the $P_I$ parameter to appear $$c = \frac{t}{P_I \frac{(R^B - R^M)}{R^M - R^V} + 1}$$

with $P_I = \frac{(D/H)_I^B}{(D/H)_I^V}$ and $(D/H) = 2 f m_f(D/H)$ if $P_I$ is close to 1, the preceding simplified expressed is found again. It should however be noted that:

(1) in the preceding expression, t and $R^M$ are measured on the ethanol extract of the chaptalized wine, but $R^V$ and $R^B$ must be considered as calibrating values. $R^V$ is the deuterium rate of the unchaptalized wine and $R^B$ that of the beet alcohol used.

Example: let us consider a 12° wine characterized by $R^M = 2.352$

On standard wines were measured $R^V = 2.485$; $R^B = 2.711$.

From which is deduced $c = 2.3°$ (2) Another possibility of using the preceding formula is to compare an unknown chaptalized wine $c_x$ with two standard wines, one unchaptalized and the other chaptalized to a known degree $c_1$ We have $c_1 = t_1 \left( \dfrac{R_0^V - R_1^M}{R_0^V - R_0^B} \right)$ $c_x = t_x \left( \dfrac{R_0^V - R_x^M}{R_0^V - R_x^M} \right)$ from where $c_x = t_x \dfrac{c_1}{t_1} \left( \dfrac{R_0^V - R_x^M}{R_0^V - R_1^M} \right)$ $R_0^V$ is measured on the control unchaptalized wine, $R_1^M$ on the control chaptalized wine with a rate $c_1$, and $R_x^M$ on the unknown wine.

Example: let us consider an unchaptalized wine $R_0^V = 2.460$ a chaptalized wine at 2.5° and with a strength of 12°, $R_1^M = 2.532$ an unknown wine at a strength of 11°, $R_x^M = 2.507$ It is deduced therefrom $$c_x = \frac{12 \times 2.5}{11} \frac{(2.460 - 2.507)}{(2.460 - 2.532)} = 1.5°$$

(3) When the chaptalization is carried out with a sugar other than beet sugar, the preceding formula remains valid. It is then sufficient to replace $R^B$, the characteristic parameter of beet, by $R^S$, which is that of unknown sugar (cane sugar, maize glucose . . . ).

Example of calculation in the case of chaptalization

Chaptalization of a white wine

A test sample of 750 ml is neutralized to pH 7.5 with NaOH 1N and a first distillation is effected with an apparatus formed of a 20 cm Vigreux column and a 25 cm West cooler. All that passes before 90° C. is collected (about 80 to 150 ml). Then the distillate is rectified with the same apparatus and 15 ml of an ethanol-water mixture is collected which boils at 78.5° and which contains 92 to 96% of ethanol. This mixture is introduced into the above-described measuring cell containing acetonitrile as standard substance. The RMN $^2$H spectrum is then recorded using the same acquisition parameters as those defined in the preceding example. FIGS. 3A and 3B show the spectra of two white wines, one unchaptalized A and the other chaptalized B. The results are expressed by using two different scales, corresponding to the heights (h) and to the surfaces (S) of the signals.

| SIGNAL | | (0) | (1) | (2) |
|---|---|---|---|---|
| A | h | 107.5 | 176.5 | 142.0 |
|   | s | 40.5 | 64.8 | 51.0 |
| B | h | 109.0 | 188.0 | 157.0 |
|   | s | 34.0 | 51.5 | 42.5 |

The following values of D(1), D(2) and R are then deduced therefrom:

|  | $D_1$ | $D_2$ | R |
|---|---|---|---|
| A (h) | 1.637 | 1.321 | 2.421 |
| B (h) | 1.725 | 1.440 | 2.504 | from which it may be concluded that B is chaptalized (Rate of chaptalization 1.5°).

Characterization of the naturally deuterated chiral molecules: application to determination of the origin of the product.

The molecules containing a —CHD— pattern may be chiral if he substituents of the —CHD— group are different. Two cases are to be considered, according as to whether there is another center of dissymetry in the molecule or not:

(a) Case where there is no other center of dissymetry in the molecule: example of the ethanol molecule CH$_3$—CHD—OH To be able to characterize the configuration of the —CHD— carbon by RMN of the deuterium, the alcohol must be transformed stereospecifically into a diastereoisomer. This may be done by reaction of the alcohol with camphanic acid (1) and subsequent addition of dipivaloylmethane europium or similar compound

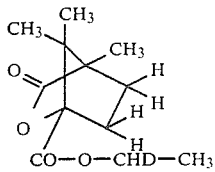
(1)

Two signals CHD(R) and CHD(S) appear in the RMN spectrum and their relative intensity gives access to the enantiomeric purity of the ethanol considered.

(b) Case where there is another center of dissymetry in the molecule: example of the molecule of an aminoacid (proline).

Proline, as in most amino-acids, contains an assymetric carbon

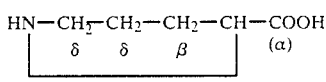

and the natural monodeuterated molecules exist in the form of diastereoisomers. The RMN spectrum of deuterium of the proline may in particular allow the diastereoisomers $(\beta_R)$ and $(\beta_S)$ and $(\delta_R)$ and $(\delta_S)$ to be identified:

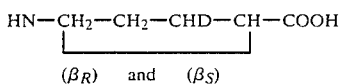

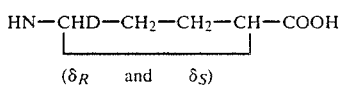

The enantiomeric purity of the $(\beta)$ and $(\delta)$ sites may be determined by measuring the ratio of the intensities of the corresponding signals and be used as identification criterium. Examples of calculation in the process for recognizing the origin of natural molecules of a given species.

1st example: Differentiation of a maize alcohol (A) and a beet alcohol (B).

A sample of industrial alcohol (96%) or alcohol extracted from an alcoholized beverage obtained by fermentation of maize (A) or by fermentation of beet molasses (B) is introduced into the above-described measuring cell containing acetonitrile as standard substance. The acquisition parameters are the following:

| Acquisition time | 6.8 s |
|---|---|
| Pulse angle | 90° |
| Scanning range | 1200 Hertz |
| Decoupling of the protons by noise | 3 watts |
| Number of pulses | 2000 |
| Exponential multiplication | 2 s |

FIGS. 2A and 2B show the spectra of the two maize (A) and beet (B) alcohols. The results are expressed in two different scales corresponding to the heights (h) and to the surfaces (s) of the signals

| SIGNAL | | (0) | (1) | (2) |
|---|---|---|---|---|
| A | h | 106.0 | 221.8 | 163.0 |
| | s | 26.8 | 44.7 | 32.4 |
| B | h | 133.5 | 206.0 | 184.0 |
| | s | 33.4 | 49.1 | 42.0 |

From which the values of D(1), D(2) and R are deduced

| | D (1) | D (2) | R |
|---|---|---|---|
| A (h) | 2.092 | 1.538 | 2.205 |
| B (h) | 1.543 | 1.378 | 2.680 |

The comparison of the values D(1), D(2) and R allow the two alcohols (A) and (B) to be identified without ambiguity. It may also be inferred therefrom that the overal deuterium content of the maize alcohol (A) is 1.060 times higher than that of the beet alcohol.

2nd Example

Identification of a mixture of alcohols of different origins in ordinary commercially available alcohols (whisky, vodka).

a blended mixture is characterized by a mixture of barley alcohol (malt) and another grain alcohol (maize for example). Let $R_{(barley)}=2.480$ and $R_{(maize)}=2.230$, which values correspond respectively to pure malt whisky and pure maize grain whisky. The value $R=2.418$ is measured for a blended whisky and so it may be stated that this whisky contains 25% of maize alcohol;

a commercial vodka is characterized by a value $R=2.627$ and it is known, following measurements on vodkas of controlled origin, that a pure wheat grain or potato vodka is defined by the value $R_{(wheat)}=2.470$ or $R_{(potato)}=2.710$. The commercial vodka contains then 65% of potato alcohol.

3rd Example

Identification of a pure barley beer and a beer prepared with a mixture of barley and raw grain (maize for example).

Bearing in mind, for barley and maize alcohol, the values $R_{(barley)}=2.480$ and $R_{(maize)}=2.230$, a beer characterized by a parameter $R=2.405$ will be considered to contain 30% of maize alcohol. A beer considered pure barley should be characterized by a value between the limits $R=2.480\pm0.02$ (in the case of the barley species considered here).

4th Example

Differentiation of anethols

Since the chemical formula of athenol is

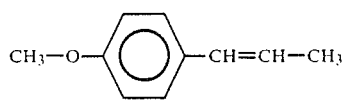

we have the six following different mono deuterated molecules (1)

$CH_2D-O-\langle\bigcirc\rangle-CH=CH-CH_3$ (2)

$CH_3-O-\langle\bigcirc\rangle-CH=CH-CH_3$
       D (3)

$CH_3-O-\langle\bigcirc\rangle-CH=CH-CH_3$
              D (4)

$CH_3-O-\langle\bigcirc\rangle-CD=CH-CH_3$ (5)

$CH_3-O-\langle\bigcirc\rangle-CH=CD-CH_3$ (6)

$CH_3-O-\langle\bigcirc\rangle-CH=CH-CH_2D$

Thus is calculated $$D'(1) = \frac{S(1)}{S(o)} \quad D'(2) = \frac{S(2)}{S(o)}, \text{ etc..}$$

and similarly $$T = \frac{S(1) + S(2) + S(3) + S(4) + S(5) + S(6)}{S_o}$$

The product is introduced directly into the above-described measuring cell containing acetonitrile as standard substance. The acquisition parameters are the same as those described in example 1.

FIGS. 4A and 4B represent the spectra of the two anethols A (natural) and B (synthetic).

| SIGNAL | (0) | (1) | (2) | (3) | (4) | (5) | (6) |
|---|---|---|---|---|---|---|---|
| h | 237.0 | 144.5 | 58.0 | 81.8 | 36.0 | 38.0 | 136.5 |
| s | 40.0 | 30.0 | 24.0 | 30 | 13.5 | 11.2 | 27.8 |
| h | 209.0 | 152.2 | 52.3 | 73.0 | 53.2 | 34.0 | 175.7 |
| s | 40.0 | 32.0 | 22.8 | 26.8 | 18.5 | 10.0 | 36.0 |

From which the previously defined values D(i) are deduced:

| | D(1) | D(2) | D(3) | D(4) | D(5) | D(6) | D(1)/D(6) |
|---|---|---|---|---|---|---|---|
| A(h) | 0.610 | 0.245 | 0.345 | 0.152 | 0.160 | 0.576 | 1.059 |
| B(h) | 0.728 | 0.250 | 0.349 | 0.255 | 0.163 | 0.841 | 0.866 |

From a consideration of the sum of the surfaces of the signals of an anethol with respect to those of the standard substance we may conclude in the existence of an overall deuterium content 1.071 times greater in B than in A. These two characteristics allow the two anethols of different origin to be identified without any ambiguity.

5th Example

Identification of the origin of a commercial or natural amino-acid or an amino-acid coming from the degradation of animal or plant proteins. Case of aspartic acid $HOCO—CH_2—CH(NH_2)COOH$.

The aspartic acid is dissolved in water free of deuterium (D/H $1.5.10^{-6}$) and the pH of the solution is brought to 12 by means of small sodium pellets. The molar fractions of the different deuterated molecules present are then measured:

| $HOCO—CHD—CH(NH_2)—COOH$ | $HOCO—CHD—CH(NH_2)—COOH$ | $HOCO—CH_2—CD(NH_2)—COOH$ |
|---|---|---|
| (R) | (S) | |
| $(\beta_R)$ | $(\beta_S)$ | $(\alpha)$ |

(the molecules containing deuterium at the exchangeable sites are not considered here).

In the case of a statistical distribution of deuterium, the molar fractions fm of the three molecules $(\beta_R)$, $(\beta_S)$ and $(\alpha)$ are equal to 0.143.

A sample obtained in the United States is characterized by the values $$fm(\beta_R) = 0.340 \; fm(\beta_S) = 0.245 \; fm(\alpha) = 0.415$$

and a sample obtained by fermentation in France $$fm(\beta_R) = 0.330 \; fm(\beta_S) = 0.300 \; fm(\alpha) = 0.370$$

The isotopic composition of the $\beta$ sites with respect to the $\alpha$ sites and the distribution of the chiral molecules $(\beta_R)$ and $(\beta_S)$ differ very significantly in the two sample which may be identified and characterized.

6th Example

Determination of the year of production or of harvesting of a sample by measuring the geoclimatic variations of the isotopic ratio R as a function of the place of production or harvesting.

A series of alcohols from beets harvested in the Pas de Calais region (F) between 1972 and 1976 is characterized by the following relationship:

$$R_C = 4.68 + 0.00264H - 0.62T$$

($R_C$ is the reduced and centered value of the $R_h$ parameter, H is the average water height of the atmospheric precipitations in the place of production and T the average temperature of the place of production during the growing months of the year considered, H in mm and T in °C.

A beet alcohol of unknown vintage is characterized by a value $R_C = 1.250$. From consultation of the National Meteorological tables for the region considered it may be deduced that the values H and T for the year 1975 give the best agreement between the calculated $R_C$ and the experimental $R_C$.

Recording of the RMN spectra

(a) Acquisition of the spectra

The resolution must be carefully adjusted in resonance $^1H$, by using the field-frequency locking channel. A spectral line width of the order of 1 hertz may then be obtained. The number of accumulations must be sufficiently great for the signal/noise ratio to be between 80 and 120; therefore, the relative quantitative measurements are optimized. 1000 to 2500 acquisitions are sufficient. Smaller values of the signal/noise ratio may also be used, but the accuracy is slightly reduced. The length of the pulse corresponds to an excitation angle of 90°.

The acquisition time must ensure good digital resolution (0.07 to 0.015 Hz per point) over a restricted range. Acquisition times of 6.8 to 13.6 seconds may be used for 600 to 1200 Hz ranges.

To improve the statistical accuracy of the measurements, it is recommended to accumulate 4000 to 6000 free induction signals and to store them on a magnetic disk in blocks of varying size (1000 to 2000) depending on the tuning of the probe.

(b) Manipulation of the free induction signal

The measurements are effected by series of 3 to 6 spectra, which are stored on a magnetic disk in the form of free induction signals.

Each signal is then transformed into a frequency spectrum, by using a variable exponentia multiplication. The spectral line must not be too fine, so as to avoid anomalies of height, nor too wide. A time constant between 0 and 4 seconds is selected. The spectrum is then digitalized in frequency, and intensity (heights and integrals), by using phase adjustment under standard conditions. A plot on paper is effected with expansion from 1 to 12 Hz/cm and with a precise scanning rate.

It is also possible to reproduce by photocopying the high density signals on paper, cutting them out and weighing them with precision, in the presence of a square of paper of constant area serving as paper density reference for each signal. In the case of wide RMN curves, the use of a planimeter is also recommended.

The signals stored by blocks are multiplied by using two different time constants, one between 0.5 and 1.5 s and the other between 1.8 and 2.5 s) and a Fournier transformation with zero filling of the unused memory words up to 32K signal is carried out. The frequency spectra are then treated in two different ways. From the list of intensities given by the computer on the absorption spectrum with standard phase adjustment and on the power spectrum, and from the spectrum recorded on paper which also allows correction of the base line of the frequencies and of the integral. A statistical treatment over 18 to 36 values of intensity is effected to obtain the average and the typical difference of the measurement population, supposed normal. For a degree of confidence of 99%, the average value of the parameter $R_h$ is contained in the limits $R_h \pm 0.005$.

When it is a question of comparing several samples of an alcohol series, factorial analysis treatment further improves the accuracy of the measurements. The data is arranged in the form of a matrix having m lines and n columns; the n columns represent the different samples, for each of which 18 to 36 measurements of the ratio $R_h$ are available (the $R_h$ ratios represent then the lines of the observation matrix). The matrix, broken down into independent factors, is then reconstructed with the first factor which corresponds to the highest eigen value, largely dominant (greater than 95%). The new values of $R_h$ thus obtained are freed of the random errors related to the measurements and allow a more sensitive comparison of the different samples of the series.

Description of a measuring cell

The measuring cell in accordance with the present invention, shown in FIG. 1, is formed from two coaxial tubes: the outer coaxial tube 10 made from calibrated Pyrex glass having an outer diameter of 15 mm and the inner coaxial tube 11 made from calibrated Pyrex glass having an outer diameter of 5 mm. This latter is shown sealed after introduction of the standard. The two tubes are separated and held firmly in place by means of Teflon seal: the upper block 15 and the lower block 16. The upper cylindrical Teflon block of an outer diameter of 13.45 mm is pierced at its center with a hole of inside diameter equal to 5 mm over the whole of its length (about 3 cm), so as to be able to house tube 11 therein. This block 15 is also pierced with two orifices 12 and 13, having an outer diameter of 2 mm and threaded over 1 cm. Orifice 12 is intended for introducing, into the lower part 17 of tube 10, the sample to be analyzed by means, for example, of a syringe and a needle. The air contained in the lower part 17 escapes through orifice 13. The innner tube 11 rests on block 16 in which is pierced a blind hole having an inner diameter of 5 mm, over a length of 2 cm, so as to house therein the lower part of tube 11.

Orifice 14 pierced in block 16 allows the air to escape from the bottom of the tube when the block descends. The hole is also threaded so as to be able to extract the block from the tube by means of a threaded rod. Blocks 15 and 16 are machined so as to produce cylindrical grooves which facilitate the Teflon-Pyrex sliding.

This cell may be perfectly suitable for quantities of liquid between 1 and 15 ml.

As is clear from the foregoing, the invention is in no wise limited to those of its embodiments and modes of implementation and application which have just been more explicitly described: it embraces, on the contrary, all the variations thereof which may occur to the technician skilled in the art, without departing from the scope or spirit of the present invention.

What is claimed is:

1. A process for the detection and quantitative and qualitative differentiation of naturally deuterated products and for detecting chaptalization of wines, comprising:

(a) preparing a standard by mixing a portion of a hydrocarbon-containing compound with another portion of the same compound which has been artificially deuterated to 95–99% to obtain an overall deuteration rate of the mixture of between 0.01 and 0.2%;

(b) introducing the standard into a measuring cell of a nuclear magnetic resonance analysis apparatus (NMR); said measuring cell capable of receiving the standard and the products to be analyzed without the occurrence of any mixing thereof;

(c) adding the product to be analyzed to the measuring cell; and (d) introducing the measuring cell into the NMR apparatus and recording a deuterium spectrum thereof which is then compared with a NMR deuterium spectrum of products of known geographical origin and known chemical and/or biochemical sources, previously prepared with the same standard.

2. The process as claimed in claim 1, wherein enantiomeric purity of alcohols contained in the products is determined by combining them chemically with an optically active compound and the resulting product is subjected to steps (b) through (d).

3. The process as claimed in claim, 1, wherein the standard is a hydrocarbon-containing compound selected from the group consisting of tetramethylsilane, hexamethyldisilane, hexamethyldisiloxane, hexamethyldisilazane, dimethyl 4,4-silapentane-4-sodium sulfonate, dimethyl-4,4-silapentane-4-sodium carboxylate, octamethylcyclotetrasiloxane, tetrakis(trimethylsilyl)methane, acetonitrile, acetone, benzene, dimethylsulfoxyde and chloroform.

4. The process as claimed in claim 1, wherein the products to be analyzed are wines, and prior to step (c), the product is neutralized to pH 7.5 with an alkali and distilled.

5. The process as claimed in claim 1, wherein the product is first dehydrated on $CaH_2$, and then distilled by liquid nitrogen cryo-trapping prior to step (c).

6. The process as claimed in claim 1, wherein between 0.01 and 1% vol/vol of an acid, selected from the group consisting of hydrochloric acid, nitric acid, sulfuric acid, phosphoric acid, trichloracetic acid and perchloric acid, is added to the product prior to step (c).

7. The process of claim 1, wherein the product to be analyzed is first dehydrated on $CaH_2$ and then distilled by liquid nitrogen cryo-trapping prior to step (c).

8. The process of claim 1 wherein between 0.01 and 1% vol./vol. of an acid selected from the group consisting of hydrochloric acid, nitric acid, sulfuric acid, phosphoric acid, trichloroacetic acid and perchloric acid, is added to the product prior to step (c).

9. The process according to claim 1, wherein there is added to the standard and/or to a sample of the product to be analyzed, small amounts of a chelate selected from the group consisting of chromium chelate, iron chelate, cobalt chelate, nickel chelate, europium chelate, praseodyme chelate, ytterbium chelates, dysprosium chelate, holmium chelate, erbium chelates and combinations thereof.

10. The process as claimed in claim 9, wherein said chelates are derived from a dione of the formula I

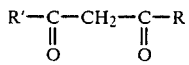

in which:
R is selected from the group consisting of $CH_3$, $tC_4H_9$, $nC_3F_7$, $C_2F_5$, $CF_3$, and $tC_4D_9$, and
R' is selected from the group consisting of $CH_3$, $tC_4H_9$, $CF_3$, $nC_3F_7$, $C_2F_5$, and $nC_3H_7$.

11. A process for the detection and quantitative and qualitative differentiation of naturally deuterated products containing alcohols and for detecting chaptalization of wines, comprising:

(a) preparing a standard comprising an intramolecular reference which is chemically combined with an alcohol;

(b) introducing the standard into a measuring cell of a nuclear magnetic resonance analysis apparatus (NMR); said measuring cell being capable of receiving the standard and the products to be analyzed without the occurrence of mixing;

(c) adding the product to be analyzed to the measuring cell; and (d) introducing the measuring cell into the NMR apparatus and recording a deuterium spectrum of the product which is compared with a NMR deuterium spectrum of products containing alcohols of known geographical origin and known chemical and/or biochemical sources prepared previously with the same standard.

12. The process as claimed in claim 11, wherein the intramolecular reference is selected from the group consisting of references formed from acetic anhydride, acetic acid, acetyl chloride, acetyl bromide and combinations thereof, which reacts with ethanol in the product to form ethyl acetate.

13. The process of claim 11 wherein the products to be analyzed are wines and prior to step (c), the product is neutralized to pH 7.5 with an alkali and distilled.

14. The process of claim 11, wherein enantiomeric purity of the alcohols contained in the products is determined by chemically combining the alcohols with an optically active compound, and subjecting the resulting product to steps (b) through (d).

15. The process as claimed in claim 14, wherein the optically active compound is selected from the group consisting of compounds formed from camphanic acid, malic acid, aspartic acid, proline, phenylalanine and combinations thereof, to which small amounts of chelates are added.

16. The process of claim 14, wherein the optically active compound is selected from the group consisting of compounds formed from camphanic acid, malic acid, aspartic acid proline phenylalanine and combinations thereof to which compound, small amounts of chelates are added.

* * * * *